(12) United States Patent
Hunter

(10) Patent No.: US 9,932,910 B2
(45) Date of Patent: Apr. 3, 2018

(54) NATURAL GAS QUALITY SENSOR AND METHOD FOR USING THE SAME

(71) Applicant: AVL Powertrain Engineering, Inc., Plymouth, MI (US)

(72) Inventor: Gary Hunter, Brighton, MI (US)

(73) Assignee: AVL Powertrain Engineering, Inc., Plymouth, MI (US)

( * ) Notice: Subject to any disclaimer, the term of this patent is extended or adjusted under 35 U.S.C. 154(b) by 316 days.

(21) Appl. No.: 14/676,964

(22) Filed: Apr. 2, 2015

(65) Prior Publication Data

US 2015/0300273 A1 Oct. 22, 2015

Related U.S. Application Data

(60) Provisional application No. 61/981,260, filed on Apr. 18, 2014.

(51) Int. Cl.
*F02D 19/02* (2006.01)
*G01N 21/59* (2006.01)
(Continued)

(52) U.S. Cl.
CPC ....... *F02D 19/029* (2013.01); *F02D 41/0027* (2013.01); *F02M 21/0218* (2013.01);
(Continued)

(58) Field of Classification Search
CPC .............. F02D 19/029; F02D 41/0027; G01N 2223/509; G01N 21/3581; G01N 21/3504
See application file for complete search history.

(56) References Cited

U.S. PATENT DOCUMENTS 7,091,487 B2 8/2006 Hodgkinson
2002/0040590 A1* 4/2002 Schley ............... G01N 21/3504
73/23.2
(Continued)

FOREIGN PATENT DOCUMENTS

DE 102007025585 A1 12/2008
DE 102011102430 A1 11/2012
(Continued)

OTHER PUBLICATIONS

Extended European Search Report for EP15163539.8, dated Sep. 21, 2015.

*Primary Examiner* — Kevin A Lathers
(74) *Attorney, Agent, or Firm* — Harness, Dickey & Pierce, P.L.C.

(57) ABSTRACT

A system and method for determining the quality of natural gas is provided. The system includes a fuel line for communicating natural gas to an engine. An infrared light source is disposed along the fuel line and is configured to emit a beam of infrared light into the fuel line having a wavelength of 6 to 10 micrometers. An infrared light detector detects a transmission value of the natural gas as the beam of infrared light passes through the fuel line. A natural gas quality module receives the transmission value from the infrared light detector and determines a quality value of the natural gas based on an amount of infrared light absorbed by methane in the natural gas. An engine control module, including a feed-forward control loop, receives the quality value from the natural gas quality module and alters an operating parameter of the engine in response thereto.

25 Claims, 3 Drawing Sheets

(51) Int. Cl.
  *G01N 21/85* (2006.01)
  *G01N 21/3504* (2014.01)
  *F02P 5/04* (2006.01)
  *F02D 37/02* (2006.01)
  *F02D 41/00* (2006.01)
  *F02M 21/02* (2006.01)
  *F02M 21/04* (2006.01)

(52) U.S. Cl.
  CPC ......... *G01N 21/3504* (2013.01); *G01N 21/59* (2013.01); *G01N 21/85* (2013.01); *F02D 19/022* (2013.01); *F02D 37/02* (2013.01); *F02D 41/0007* (2013.01); *F02D 41/0025* (2013.01); *F02D 2041/001* (2013.01); *F02D 2200/06* (2013.01); *F02D 2200/0602* (2013.01); *F02D 2200/0606* (2013.01); *F02D 2200/0611* (2013.01); *F02D 2200/0612* (2013.01); *F02M 21/0209* (2013.01); *F02M 21/04* (2013.01); *F02P 5/045* (2013.01); *Y02T 10/32* (2013.01)

(56) References Cited

U.S. PATENT DOCUMENTS

| | | |
|---|---|---|
| 2009/0120385 A1 | 5/2009 | Munshi et al. |
| 2012/0210988 A1* | 8/2012 | Willi .................. F02D 19/024 123/575 |
| 2014/0152977 A1 | 6/2014 | Ranftl et al. |

FOREIGN PATENT DOCUMENTS

| | | |
|---|---|---|
| EP | 1070955 A2 | 1/2001 |
| EP | 2472249 A1 | 4/2012 |
| JP | 2004-77131 A * | 3/2004 |
| WO | 9825128 A1 | 6/1998 |
| WO | 2014020231 A1 | 2/2014 |

* cited by examiner

NATURAL GAS QUALITY SENSOR AND METHOD FOR USING THE SAME

CROSS-REFERENCE TO RELATED APPLICATIONS

This application claims the benefit of U.S. Provisional Application No. 61/981,260, filed on Apr. 18, 2014. The entire disclosure of the above application is incorporated herein by reference.

FIELD

The present disclosure relates to fuel systems and to methods of controlling an engine. More particularly, the present disclosure relates to engines that run on natural gas fuels and associated fuel systems and engine control methods capable of determining the quality of the natural gas being supplied to the engine.

BACKGROUND

This section provides background information related to the present disclosure which is not necessarily prior art.

Natural gas fueled engines are gaining popularity as an environmentally friendly alternative to petroleum based fuels such as gasoline and diesel fuel. Natural gas is generally regarded as being better for the environment because engines running on natural gas generally have reduced emissions and natural gas is more abundant than petroleum.

Natural gas is a naturally occurring hydrocarbon mixture containing primarily methane. The methane content significantly contributes to the combustion characteristics of natural gas and hence its quality. However, natural gas also contains smaller percentages of other hydrocarbons, carbon dioxide, nitrogen, water vapor, and hydrogen sulfide. The composition of natural gas varies widely depending on the geographic origin of the natural gas and the amount of time that has passed since it was extracted. The composition of natural gas also varies depending on whether the natural gas comes from a well head, a landfill, or other bio-mass derivatives. As a result, natural gas has widely varying combustion characteristics.

In addition to its use as a fuel to power engines, natural gas is widely used for residential and commercial heating, cooking, and power generation. In the residential and commercial industry setting, methods and equipment have been developed for measuring the caloric value of natural gas and its flammability limits due to the wide variances in composition. However, developments allowing for real-time quality determination of the natural gas being injected into engines have been slow to materialize.

Natural gas can have widely varying energy content and knock resistance properties depending on the concentration of various components in the fuel. These variations can have a severe impact on the operation of natural gas fueled engines and can cause high degrees of cyclic combustion variability, mis-fire, low performance, and engine knock. These are unwanted operating conditions which can degrade the performance, reliability, and service life of natural-gas engines. What is needed is a system and method for determining the quality of natural gas as it flows through an engine's fuel system to enable the real-time adjustment of operating parameters of the engine.

SUMMARY

This section provides a general summary of the disclosure, and is not a comprehensive disclosure of its full scope or all of its features.

Generally, a fuel system and method is provided for determining the quality of the natural gas being supplied to an engine and making the appropriate adjustments to the operating parameters of the engine.

In one form, the present disclosure provides a system for determining the quality of natural gas being delivered to the engine through at least one fuel line. The at least one fuel line may have a fuel line wall defining an inner diameter. A sensor assembly is disposed along the fuel line wall. The sensor assembly includes an infrared light source that emits a beam of infrared light into the at least one fuel line along an optical path extending across the inner diameter of the at least one fuel line. The sensor assembly also includes an infrared light detector that detects a transmission value of the beam of infrared light as it passes through the natural gas in the at least one fuel line. The infrared light source includes at least one light emitting diode that emits a beam of infrared light having a wavelength ranging between and including 6 micrometers and 10 micrometers. The sensor assembly further includes a natural gas quality module for receiving the transmission value from the infrared light detector to determine a quality value of the natural gas based on an amount of the beam of infrared light absorbed by methane in the natural gas. The system may also include an engine control module. The engine control module includes a feed-forward control loop that receives the quality value of the natural gas from the natural gas quality module and alters an operating parameter of the engine in response to the quality value of the natural gas. In some examples, the at least one fuel line may interconnect a pressure regulator and a fuel accumulator of the fuel system.

In another form, the disclosure provides a method for controlling an engine fueled by natural gas. The method includes the step of providing at least one fuel line for communicating natural gas to the engine where the at least one fuel line has an inner diameter. The method also includes the steps of emitting a beam of infrared light into the at least one fuel line along an optical path that extends across the inner diameter of the at least one fuel line and detecting a transmission value of the beam of infrared light after it has passed through the inner diameter of the at least one fuel line. The method further includes the step of determining an amount of the beam of infrared light absorbed by methane in the natural gas in response to detecting the transmission value of the beam of infrared light. The method also provides for determining a quality value of the natural gas in response to the amount of the beam of infrared light absorbed by the methane in the natural gas. The method may also include the step of altering an operating parameter of the engine in a feed-forward loop in response to the quality value of the natural gas. In accordance with this method, the beam of infrared light that is emitted into the at least one fuel line may have a wavelength ranging between and including 6 micrometers and 10 micrometers.

Accordingly, the system and method disclosed herein achieve several advantages. The system and the method determines the quality of natural gas as it flows through the at least one fuel line on its way to being injected into the engine. The placement of the sensor assembly and the feed-forward control loop of the engine control module enable real-time adjustments of operating parameters of the engine. As such, the engine control module can tailor the operating parameters of the engine to the quality of the natural gas being injected into the engine. This allows for operation of natural gas engines without the high degrees of cyclic combustion variability, misfire, low performance, and engine knock typically experienced as a result of inconsistent natural gas compositions.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure, wherein.

Corresponding reference numerals indicate corresponding parts throughout the several views of the drawings.

DETAILED DESCRIPTION

Figure 1:
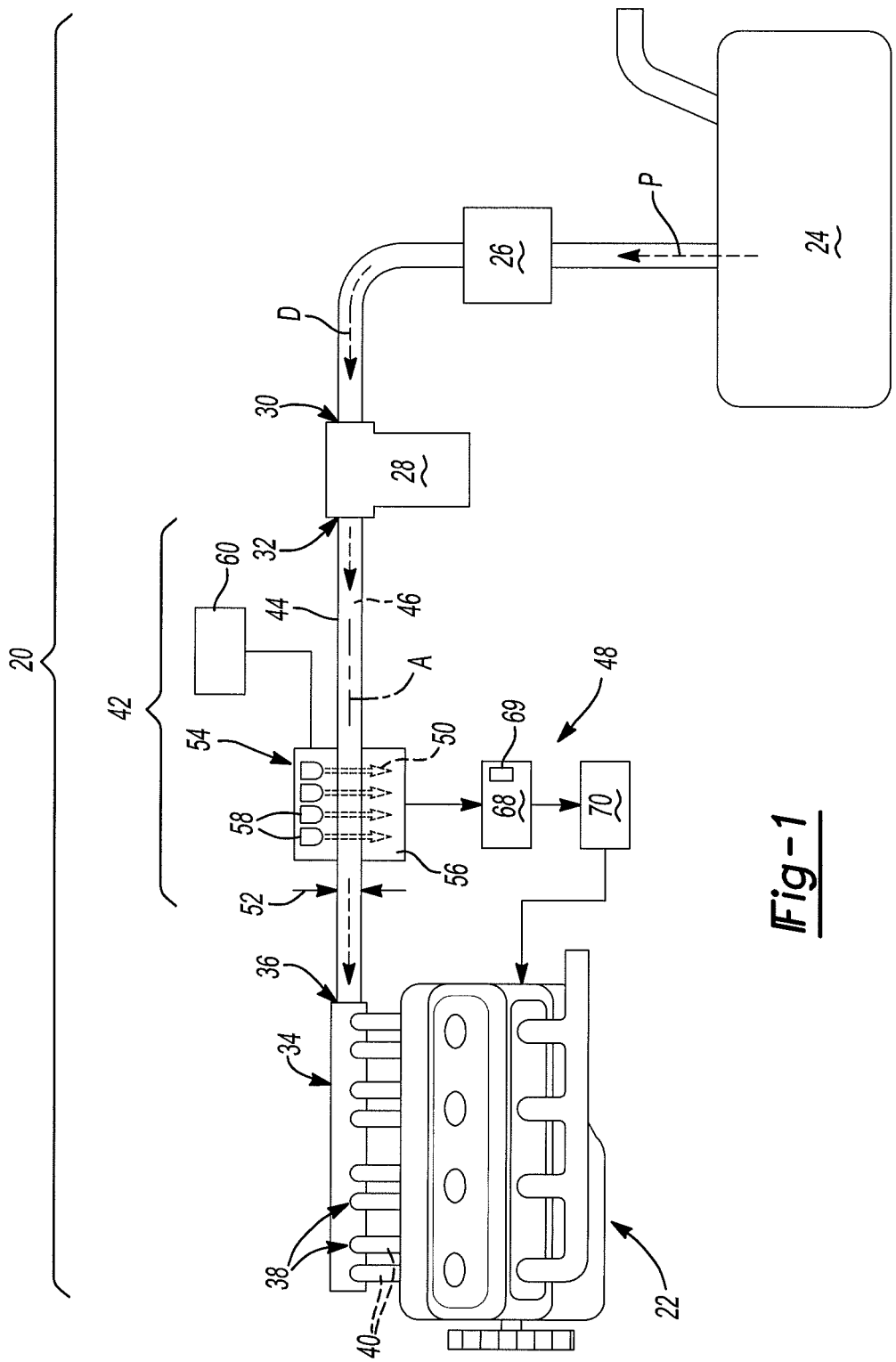
FIG. 1 is a schematic diagram of an exemplary fuel system including the sensor assembly described by the present disclosure.

Example embodiments are provided herein with reference to the accompanying drawings so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 2:
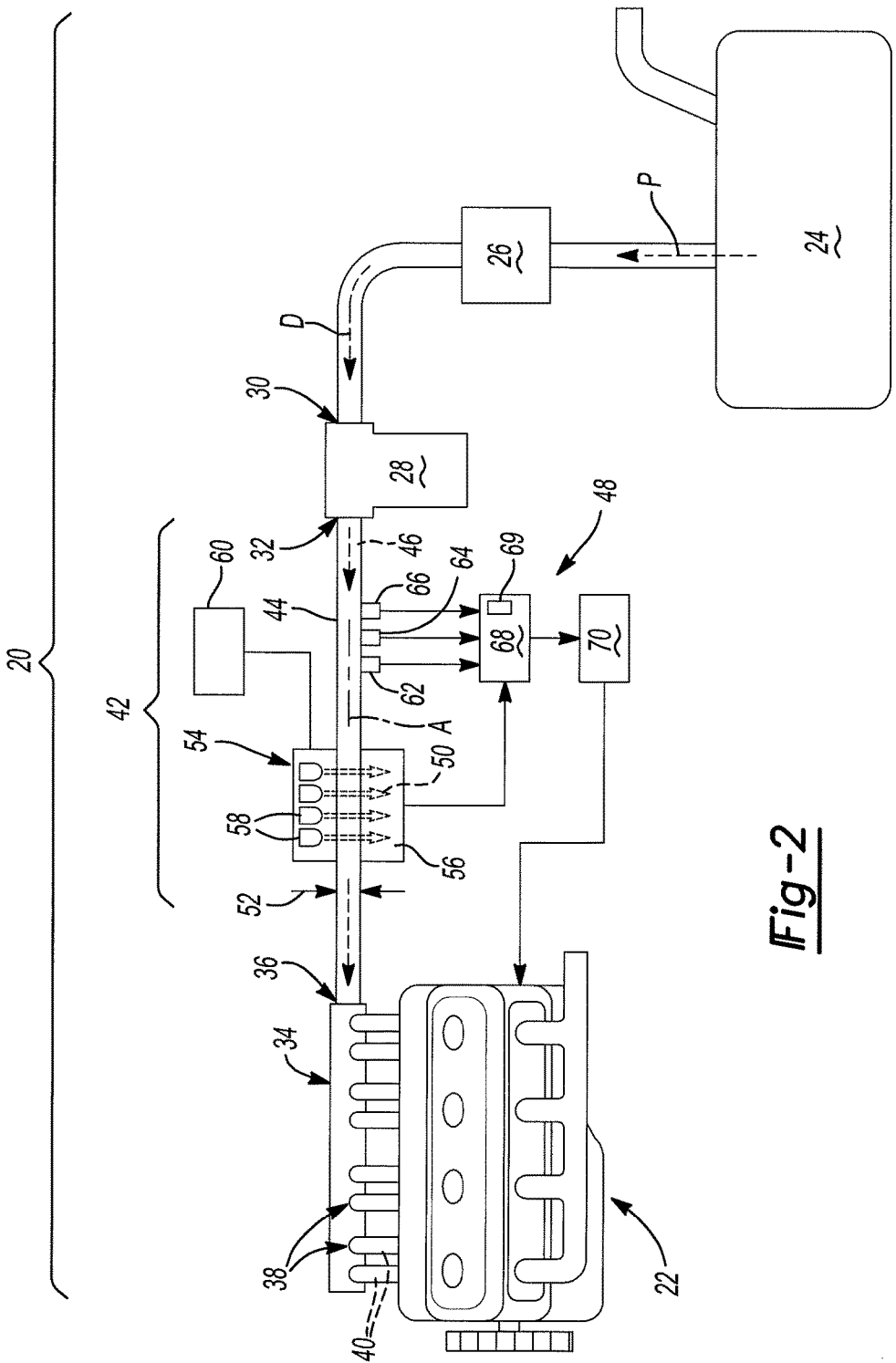
FIG. 2 is a schematic diagram of another exemplary fuel system including an optional water vapor sensor, temperature sensor, and pressure sensor described by the present disclosure.

Referring to the FIGS. 1 and 2, wherein like numerals indicate corresponding parts throughout the several views, a fuel system 20 for supplying a natural gas to an engine 22 is provided. The fuel system 20 may generally include a fuel tank 24 configured for holding a natural gas fuel. Such fuels are commonly known in the industry and may be, for example, compressed natural gas (CNG). Natural gas is a naturally occurring hydrocarbon mixture containing primarily methane. The methane content significantly contributes to the combustion characteristics of natural gas and hence its quality. However, natural gas also contains smaller percentages of other hydrocarbons, carbon dioxide, nitrogen, water vapor, and hydrogen sulfide. The composition of natural gas can vary widely depending on the geographic origin of the natural gas and the amount of time that has passed since it was extracted. The composition of natural gas also varies depending on whether the natural gas comes from a well head, a landfill, or other bio-mass derivatives. This is problematic to the operation of natural gas engines because the combustion characteristics vary with composition.

Depending on the natural gas fuel used and the configuration of the fuel tank 24, a fuel pump 26 may be provided. Where the fuel system 20 includes a fuel pump 26, the fuel pump 26 is placed in fluid communication with the fuel tank 24 and functions to pump the natural gas from the fuel tank 24, through the fuel system 20, and to the engine 22.

A pressure regulator 28 is typically connected in fluid communication with the fuel pump 26 or the fuel tank 24 directly where a fuel pump 26 is not required. The pressure regulator 28 has an inlet 30 that receives the natural gas from either the fuel pump 26 or directly from the fuel tank 24. The pressure regulator 28 further includes an outlet 32 that delivers the natural gas at and a predetermined pressure.

Accordingly, the pressure regulator 28 maintains the natural gas supplied by the outlet 32 at the predetermined pressure. The predetermined pressure is set for a particular application and may be selected according to the characteristics and requirements of the engine 22. A fuel accumulator 34 is disposed in fluid communication with the pressure regulator 28 to receive natural gas therefrom at the predetermined pressure. More particularly, the fuel accumulator 34 has an intake port 36 and one or more injector ports 38. The intake port 36 receives the natural gas from the pressure regulator 28. The fuel system 20 further includes one or more fuel injectors 40 that are disposed in the injector ports 38 of the fuel accumulator 34. Typically, the fuel accumulator 34 has one injector port 38 for every one fuel injector 40. The fuel injectors 40 are thus placed in fluid communication with the fuel accumulator 34 and function to inject the natural gas into the engine 22 for combustion. It should be appreciated that the fuel accumulator 34 may be a fuel rail 34. However, the term fuel accumulator 34 has been used more broadly herein because it is not intended to be limited to the linear, rail-like form of a traditional fuel rail 34. Rather, the term fuel accumulator 34 is not intended to correspond to a particular geometry.

One or more fuel lines 42 connect the pressure regulator 28 and the fuel accumulator 34. Thus, the fuel line 42 communicates the natural gas from the pressure regulator 28 to the fuel accumulator 34. More specifically, the fuel line 42 is connected to and spans a distance between the outlet 32 of the pressure regulator 28 and the intake port 36 of the fuel accumulator 34. In a configuration not shown, the pressure regulator 28 may be directly connected to the fuel accumulator 34. In this configuration, the fuel line 42, may be integrally formed as a passageway in either the pressure regulator 28 or the fuel accumulator 34. The fuel line 42 generally has a tubular shape and includes a fuel-line wall 44 defining an inner diameter 46. The inner diameter 46, as the term is used herein, describes a generally cylindrical space interior of and defined by the fuel line wall 44. As such, the inner diameter 46 has a central axis A extending co-axially with the fuel line 42 in the longitudinal direction.

Still referring to FIGS. 1 and 2, the aforesaid components of the fuel injector 40 system define a flow path P along which the natural gas is communicated from the fuel tank 24 to the engine 22. Specifically, the natural gas flows from the fuel tank 24, through the optional fuel pump 26, and to the inlet 30 of the pressure regulator 28. The natural gas flows through the pressure regulator 28 from the inlet 30 to the outlet 32 where it is delivered at the predetermined pressure. Next, the natural gas flows from the outlet 32 of the pressure regulator 28 to the intake port 36 of the fuel accumulator 34 via the fuel line 42. From the intake port 36 of the fuel accumulator 34, the natural gas flows to the injector ports 38 where the natural gas is drawn into the fuel injectors 40 and then discharged into the engine 22. Typically, the fuel injectors 40 inject the natural gas into the air intake of the engine 22 or directly into the cylinders of the engine 22.

Within the fuel line 42, the natural gas flows from the pressure regulator 28 to the fuel accumulator 34. A flow direction is generally denoted as D which comprises a vector. In the fuel line 42, the flow direction D of the natural gas generally is parallel with the central axis A of the inner diameter 46 of the fuel line 42 and points towards the direction of the fuel accumulator 34. The magnitude of the flow direction D vector represents a flow rate of the natural gas, which has several variables including, but not limited to, the size of the inner diameter 46 of the fuel line 42, the predetermined pressure of the natural gas supplied by the pressure regulator 28, friction losses, and the operation of the fuel injectors 40 (i.e. the fuel consumption of the engine 22).

The fuel system 20 further includes a sensor assembly 48. The sensor assembly 48 provides a real-time determination of a quality value of the natural gas fuel by measuring the amount of infrared light that is absorbed by the natural gas flowing through a given segment of the fuel system 20. This quality value can then be used to adjust one or more operating parameter of the engine 22. More details of the quality value and operating parameters will be discussed below.

Preferably, the sensor assembly 48 is disposed along the fuel line 42. Placement along the fuel line 42 is advantageous because this location is far enough upstream of the engine 22 to provide sufficient time to determine the quality value and make a feed-forward adjustment to one or more operating parameters of the engine 22 before the sampled natural gas reaches the fuel injectors 40. It should be appreciated that systems analyzing combustion characteristics in the cylinder lag behind the flow of natural gas through the fuel system 20. An advantage of the disclosed system is that one or more of the operating parameters of the engine 22 can be altered in response to a determined quality value of the natural gas as the sampled natural gas enters the cylinder—not after it has been combusted. In this way, the disclosed system does not rely on information concerning past combustion events to estimate the combustion characteristics of the natural gas currently being injected into the engine 22.

The sensor assembly 48 is disposed along the fuel line wall 44 and is configured to emit a beam of infrared light 50 into the fuel line 42 along an optical path 52 that extends across the inner diameter 46 of the fuel line 42. The beam of infrared light 50 is used for detecting the quality value of the natural gas in the fuel line 42. It should be appreciated that the optical path 52 generally extends entirely across the inner diameter 46 of the fuel line 42 so as to bisect the inner diameter 46. It should also be appreciated that the optical path 52 may generally be orthogonal to flow direction D of the natural gas moving through the inner diameter 46 of the fuel line 42.

The sensor assembly 48 includes an infrared light source 54 that emits the beam of infrared light 50 along the optical path 52. The sensor assembly 48 also includes an infrared light detector 56 positioned along the optical path 52 that detects a transmission value of the beam of infrared light 50. The transmission value corresponds to a measurable quantity of infrared light that is incident on the infrared light detector 56. Detection of the transmission value is made possible by the application of Beer-Lambert's law, which relates the attenuation of light to properties of the medium through which the light is traveling. In accordance with the disclosed embodiments shown in FIGS. 1 and 2, both the infrared light source 54 and the infrared light detector 56 may extend through the fuel line wall 44 at radially opposing positions such that the infrared light source 54 is within a line of sight of the infrared light detector 56. In some arrangements, the line of sight of the infrared light detector 56 may be parallel to or overlap with the optical path 52.

The infrared light source 54 may include one or more light emitting diodes (LEDs) 58 that are configured to emit the beam of infrared light 50. More specifically, the infrared light source 54 may be configured to emit a beam of infrared light 50 having a wavelength ranging between and including 6 micrometers and 10 micrometers. This terminology is used throughout the disclosure and the claims and is intended to include wavelengths of 6 micrometers and 10 micrometers and all values therebetween. Experimentation has shown the above specified wavelength range to be suitable because it envelops the 7.7 to 7.8 micrometer infrared absorption band for methane. Experimentation has also shown that spectral interference in the fuel line 42 is low within the above specified wavelength range to allow for sampling from a "clean" band of wavelengths that exhibit minimal interference. This increases the accuracy and consistency of the sensor assembly 48 as it is used in the fuel system 20 disclosed.

The infrared light source 54 may also include a power supply 60 that is electrically connected to the infrared light source 54 and more particularly to the one or more light emitting diodes 58. Accordingly, the power supply 60 supplies electricity to the infrared light source 54. Depending on the application, it is envisioned that the power supply 60 may supply either AC electricity or DC electricity to the infrared light source 54. It should be appreciated that the desired 6 micrometers to 10 micrometers wavelength range may be achieved by selecting a particular infrared light source 54 such as a particular light emitting diode 58 and/or using the power supply 60 to supplying a particular type of electricity at a particular power, voltage, current, and/or frequency.

As shown in FIG. 2, the sensor assembly 48 may optionally include a water vapor sensor 62 for detecting a water vapor concentration value of the natural gas. The water vapor sensor 62 measures the humidity of the natural gas, or in other words, the water content of the natural gas. Where the water vapor sensor 62 is not included, the water vapor concentration value of the natural gas can either be ignored or estimated. However, the accuracy of the quality value is increased when the water vapor concentration value is accounted for because water vapor in the natural gas also absorbs infrared light. Optionally, the sensor assembly 48 may also include a temperature sensor 64 and a pressure sensor 66, both of which may be disposed along the fuel line 42 adjacent the infrared light detector 56. The temperature sensor 64 detects a temperature value of the natural gas flowing past the infrared light detector 56. Similarly, the pressure sensor 66 detects a pressure value of the natural gas flowing past the infrared light detector 56.

The sensor assembly 48 may include a natural gas quality module 68 that may be electrically connected to the infrared light detector 56 and optionally to the water vapor pressure sensor 66, the temperature sensor 64, and the pressure sensor 66 when these components are included as part of the sensor assembly 48. The natural gas quality module 68 receives the transmission value from the infrared light detector 56. Optionally, the natural gas quality module 68 may receive the water vapor concentration value from the water vapor pressure sensor 66 or may store a predetermined water vapor concentration value. The natural gas quality module 68 may also receive the temperature value from the temperature sensor 64 and the pressure value from the pressure sensor 66, and determine the density of the natural gas flowing past the infrared light detector 56 based on these temperature and pressure values. The density and water vapor concentration values may be used by the natural gas quality module 68 to compensate for their respective contributions to infrared absorption.

In real-time, the natural gas quality module 68 uses the transmission value, the density of the natural gas, and optionally the water vapor concentration value to determine the quality value of the natural gas. This determination is based on the amount of the beam of infrared light 50 that is absorbed by methane in the natural gas. For example, the amount of infrared light that is emitted from the infrared light source 54 may be compared to the transmission value measured by the infrared light detector 56 to determine the amount or portion of the beam of infrared light 50 that was absorbed by the natural gas passing through the fuel line 42 in the region of the sensor assembly 48.

The natural gas quality module 68 may receive a signal from the infrared light source 54 indicating the amount of infrared light 50 emitted from the infrared light source 54. Alternatively, the amount of infrared light 50 that is emitted from the infrared light source 54 may be predetermined and may be part of the design specifications of the infrared light source 54. Further, the amount of infrared light 50 that is emitted from the infrared light source 54 can be verified by testing. For example, the infrared light source 54 can be calibrated when there is no natural gas in the fuel line 42. The quality value of the natural gas can then be determined by additional calculations or look-up tables.

In accordance with one configuration of the sensor assembly 48, the natural gas quality module 68 includes memory 69. The memory 69 of the natural gas quality module 68 stores one or more look-up tables for use in determining the quality value of the natural gas. The look-up tables correlate a plurality of amounts of infrared light absorbed by methane in natural gas to a plurality of quality values of natural gas. The natural gas quality module compares the amount of the beam of infrared light absorbed by the methane in the natural gas to the plurality of amounts of infrared light absorbed by methane in natural gas contained in the look-up table and identifies a corresponding value. Then the natural gas quality module 68 determines the quality value of the natural gas using the correlation provided in the look-up table. It should be appreciated that the look-up table may be populated with values through experimental testing and/or calculation.

The quality value of the natural gas that is determined by the natural gas quality module 68 may be indicative of various properties of the natural gas. Of particular importance in this application are properties influencing the combustion characteristics of the natural gas being supplied to the engine 22. Generally, the quality value correlates with transmission value and/or the amount of infrared light that is absorbed by the natural gas. The natural gas quality module 68 utilizes this correlation or relationship to determine the quality value sought. By way of example, the quality value that is determined by the natural gas quality module 68 may be, but is not limited to, the methane concentration of the natural gas, the energy content of the natural gas, the knock resistance of the natural gas, and the stoichiometry requirements of the natural gas. The methane concentration is the amount, proportion, or percentage of methane in the natural gas. The energy content is a numeric value expressing an amount of energy that combustion of a given quantity of the natural gas may yield. The knock resistance is a value expressing the natural gas's resistance to produce knock within the engine 22. Knock may be defined as an unwanted combustion condition that is caused by the explosion of one or more pockets of air/fuel mixture within the cylinder, where these explosions are outside the normal combustion profile for the engine 22. The stoichiometry requirements of the natural gas may be defined as the optimal set of conditions required for combustion of the natural gas, which may include the relative concentrations of chemical reactants such as the air/fuel mixture.

Still referring to FIGS. 1 and 2, the fuel system 20 may also include an engine control module 70 that may be electrically connected to the natural gas quality module 68 of the sensor assembly 48. In various implementations, the natural gas quality module 68 may be included in the engine control module 70. The fuel system 20 may include a feed-forward control loop that receives the quality value of the natural gas from the natural gas quality module 68 and alters one or more operating parameters of the engine 22 in response to the quality value of the natural gas. Adjustments of the operating parameters may change a variety of different engine operating characteristics. Generally, the operating parameters are settings that are influenced by the quality value of the natural gas being injected into the engine 22. Thus, the engine control module 70 sets or alters the operating parameters based upon their relationship with the quality value received from the natural gas quality module 68. By way of example, the one or more operating parameters that are set or altered by the engine control module 70 may include, but are not limited to, a fuel-to-air ratio of the engine 22, fuel pressure such as the predetermined pressure, ignition timing of the engine 22, valve timing of the engine 22, and/or boost pressure. The fuel-to-air ratio is the proportional value representing the mixture of natural gas and air provided to the cylinder(s) of the engine 22. The fuel pressure may be the predetermined pressure supplied by the pressure regulator 28. The ignition timing may be the timing sequence controlling the energization of a spark plug (not shown) or glow plug (not shown) of the engine 22. The valve timing may be the timing sequence controlling the opening and closing of intake and exhaust valves (not shown) of the engine 22. The boost pressure is the amount of pressure added to the air intake charge of the engine 22 by a turbine such as, but not limited to, an exhaust driven turbocharger (not shown) or a belt driven supercharger (not shown).

Advantageously, the feed-forward control loop and the positioning of the sensor assembly 48 along the flow path P allows the engine control module 70 to alter the operating parameters of the engine 22 as the sampled natural gas enters the engine 22. Accordingly, in various implementations, the engine control module 70 tailors the operating parameters to the quality value of the natural gas that is currently being injected into the engine 22 and not in response to the quality of the natural gas that was combusted during the last combustion stroke. This is beneficial because the quality of the natural gas being injected into the engine 22 can continuously vary so feed-forward adjustments are preferable to adjustments made based on natural gas that has already been run through the engine 22.

With respect to the natural gas quality module 68 and the engine control module 70, it should be appreciated that the term module may be replaced with the term circuit. The term module may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip. The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

A method for controlling an engine fueled by natural gas is also disclosed, the steps of which describe the use of the fuel system 20 described above. Now referring to FIG. 3, at step 100, the method provides at least one fuel line 42 that interconnects a pressure regulator 28 and a fuel accumulator 34 and that communicates natural gas to the engine 22. In accordance with this step, the fuel line 42 has a tubular shape and an inner diameter 46. The method also includes the step illustrated by block 102 of emitting a beam of infrared light 50, which has a wavelength ranging between and including 6 micrometers and 10 micrometers, into the fuel line 42 along an optical path 52 that extends across the inner diameter 46 of the fuel line 42.

The method further includes the step illustrated by block 104 of detecting a transmission value of the beam of infrared light 50 after it has passed through the inner diameter 46 of the fuel line 42. The method optionally includes the step illustrated by block 106 of detecting a water vapor concentration value and a density of the natural gas in the fuel line 42. As was explained in more detail above, the water vapor concentration value of the natural gas may alternatively be ignore or estimated. Also, as explained above, the density of the natural gas in the fuel line 42 may be determined based on, for example, a measured temperature value and a measured pressure value of the natural gas.

The method continues with the step illustrated by block 108 of determining an amount of the beam of infrared light 50 absorbed by methane in the natural gas based on the transmission value of the beam of infrared light 50 and optionally the water vapor concentration value and the density of the natural gas in the fuel line 42. As explained in more detail above, this step may include comparing the transmission value detected to the known amount of infrared light that is emitted into the fuel line 42. The method further includes the step illustrated by block 110 of determining a quality value of the natural gas based on the amount of the beam of infrared light 50 absorbed by methane in the natural gas and the step illustrated by block 112 of altering an operating parameter of the engine 22 in a feed-forward loop in response to determining the quality value of the natural gas. As discussed above in greater detail, the step of determining the quality value of the natural gas may include comparing the amount of the beam of infrared light absorbed by the methane in the natural gas to values contained in a look-up table and correlating the amount of the beam of infrared light absorbed by the methane in the natural gas to the values contained in the look-up table.

Figure 3:
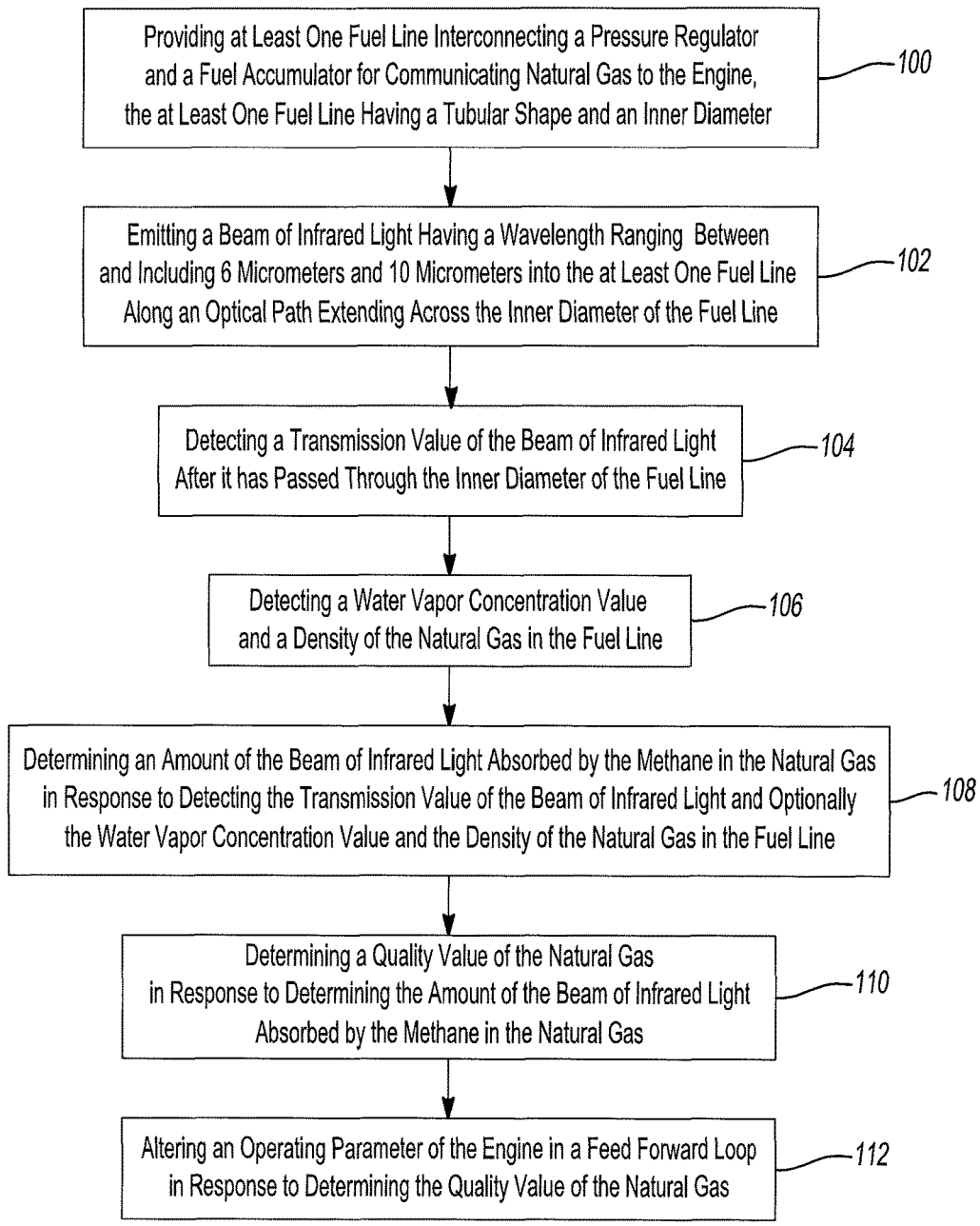
FIG. 3 is a block diagram illustrating the steps of an exemplary method for using the sensor assembly described by the present disclosure.

The method described herein and illustrated in FIG. 3 is presented for the purpose of illustration and disclosure. As evinced by the appended claims, the method is not limited to all of the steps described herein and illustrated as blocks 100 through 112 in FIG. 3. Accordingly, the method may be successfully practiced by performing only some of these steps. Additionally, the method is not limited to the order of the steps disclosed herein and illustrated in FIG. 3. The method may be practiced by performing these steps in an alternative order or sequence. As described in greater detail above, the term fuel accumulator 34 as used in the method is broader than, but includes the structure of a fuel rail. Consistent with the disclosure above, the term quality value of the natural gas, as used in the method, may denote methane concentration, energy content, knock resistance, or stoichiometry requirements of the natural gas. Similarly, the term operating parameter, as used in the method, may denote fuel-to-air ratio, fuel pressure such as the predetermined pressure supplied by the pressure regulator 28, ignition timing, valve timing, and/or boost pressure of the engine 22.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A fuel system for supplying natural gas to an internal combustion engine, comprising:
    at least one fuel line for communicating the natural gas to the internal combustion engine, said at least one fuel line having a fuel line wall defining an inner diameter; and
    a sensor assembly including an infrared light source and an infrared light detector that are disposed along said fuel line wall where said infrared light source is configured to emit a beam of infrared light into said at least one fuel line along an optical path extending across said inner diameter of said at least one fuel line and where said infrared light detector is configured to detect a transmission value of said beam of infrared light,
    wherein said infrared light source and said infrared light detector extend through said fuel line wall and radially oppose one another.

2. The fuel system as set forth in claim 1 wherein said sensor assembly includes a natural gas quality module that receives said transmission value from said infrared light detector and determines a quality value of the natural gas based on an amount of said beam of infrared light absorbed by methane in the natural gas.

3. The fuel system as set forth in claim 2 further comprising:
    an engine control module that receives said quality value of the natural gas from said natural gas quality module and alters an operating parameter of the internal combustion engine in response to said quality value of the natural gas.

4. The fuel system as set forth in claim 3 wherein said operating parameter altered by said engine control module includes at least one of a fuel-to-air ratio of the internal combustion engine, a fuel pressure supplied to the internal combustion engine, an ignition timing of the internal combustion engine, a valve timing of the internal combustion engine, and a boost pressure of the internal combustion engine.

5. The fuel system as set forth in claim 3 wherein said engine control module is electrically connected to said natural gas quality module of said sensor assembly.

6. The fuel system as set forth in claim 2 wherein said natural gas quality module is electrically connected to said infrared light detector.

7. The fuel system as set forth in claim 2 wherein said sensor assembly includes a water vapor sensor for detecting a water vapor concentration value of the natural gas, a temperature sensor for detecting a temperature value of the natural gas, and a pressure sensor for detecting a pressure value of the natural gas and wherein said natural gas quality module receives said water vapor concentration value, said temperature value, and said pressure value and determines said quality value of the natural gas based on said water vapor concentration value, said temperature value, and said pressure value.

8. The fuel system as set forth in claim 2 wherein said quality value determined by said natural gas quality module includes at least one of a methane concentration of the natural gas, an energy content of the natural gas, a knock resistance of the natural gas, and a stoichiometry requirement of the natural gas.

9. The fuel system as set forth in claim 1 wherein said at least one fuel line interconnects a pressure regulator and a fuel accumulator.

10. The fuel system as set forth in claim 9 wherein said fuel accumulator includes a fuel rail.

11. The fuel system as set forth in claim 1 wherein said infrared light source has at least one light emitting diode for emitting said beam of infrared light and a power supply electrically connected to said at least one light emitting diode for supplying electricity thereto.

12. The fuel system as set forth in claim 1 wherein said beam of infrared light has a wavelength ranging between and including 6 micrometers and 10 micrometers.

13. A system for determining the quality of natural gas, comprising:
    a sensor assembly including an infrared light source and an infrared light detector that are disposed along a fuel line of an internal combustion engine, said fuel line having a fuel line wall, where said infrared light source is configured to emit a beam of infrared light into said fuel line along an optical path extending across an inner diameter of said fuel line and where said infrared light detector is configured to detect a transmission value of said beam of infrared light; and
    a natural gas quality module that receives said transmission value from said infrared light detector and that determines a quality value of the natural gas based on an amount of said beam of infrared light absorbed by methane in the natural gas,
    wherein said infrared light source and said infrared light detector extend through said fuel line wall and radially oppose one another.

14. The system as set forth in claim 13 further comprising:
    an engine control module that receives said quality value of the natural gas from said natural gas quality module and alters an operating parameter of the internal combustion engine in response to said quality value of the natural gas.

15. The system as set forth in claim 13 wherein said infrared light source includes at least one light emitting diode configured to emit said beam of infrared light, said beam of infrared light having a wavelength ranging between and including 6 micrometers and 10 micrometers.

16. The system as set forth in claim 13 wherein said fuel line interconnects a pressure regulator and a fuel accumulator.

17. The system as set forth in claim 16 wherein said fuel accumulator is a fuel rail.

18. The system as set forth in claim 13 wherein said natural gas quality module of said sensor assembly has memory storing at least one look-up table and wherein said natural gas quality module determines said quality value of the natural gas by comparing said transmission value detected by said infrared light detector to values contained in said at least one look-up table.

19. A method for controlling an internal combustion engine fueled by natural gas, comprising the steps of:
   emitting a beam of infrared light into at least one fuel line along an optical path extending across the inner diameter of the at least one fuel line;
   detecting a transmission value of the beam of infrared light after the beam has passed through the inner diameter of the at least one fuel line and natural gas in the at least one fuel line;
   detecting a water vapor concentration value and a density of the natural gas in the fuel line;
   determining an amount of the beam of infrared light absorbed by methane in the natural gas based on the transmission value of the beam of infrared light, the water vapor concentration value, and the density of the natural as in the at least one fuel line; and
   determining a quality value of the natural gas based on the amount of the beam of infrared light absorbed by the methane in the natural gas.

20. The method of claim 19 further comprising:
   altering an operating parameter of the internal combustion engine based on the quality value of the natural gas.

21. The method of claim 20 wherein the operating parameter includes at least one of a fuel-to-air ratio of the internal combustion engine, a fuel pressure supplied to the internal combustion engine, an ignition timing of the internal combustion engine, a valve timing of the internal combustion engine, and a boost pressure of the internal combustion engine.

22. The method of claim 19 wherein the beam of infrared light that is emitted into the at least one fuel line has a wavelength ranging between and including 6 micrometers and 10 micrometers.

23. The method of claim 22 wherein said step of determining the quality value of the natural gas includes comparing the amount of the beam of infrared light absorbed by the methane in the natural gas to values contained in a look-up table and correlating the amount of the beam of infrared light absorbed by the methane in the natural gas to the values contained in the look-up table.

24. The method of claim 19 wherein said step of determining the amount of the beam of infrared light absorbed by the methane in the natural gas includes comparing the transmission value detected to a predetermined amount of infrared light emitted into the at least one fuel line.

25. The method of claim 19 wherein the quality value includes at least one of a methane concentration of the natural gas, an energy content of the natural gas, a knock resistance of the natural gas, and a stoichiometry requirement of the natural gas.

\* \* \* \* \*

UNITED STATES PATENT AND TRADEMARK OFFICE
CERTIFICATE OF CORRECTION

PATENT NO. : 9,932,910 B2
APPLICATION NO. : 14/676964
DATED : April 3, 2018
INVENTOR(S) : Gary Hunter Page 1 of 1

It is certified that error appears in the above-identified patent and that said Letters Patent is hereby corrected as shown below:

In the Claims

Column 13
Line 25, Claim 19        delete "as" and insert --gas--.

Signed and Sealed this
Twenty-sixth Day of June, 2018

Andrei Iancu
*Director of the United States Patent and Trademark Office*